(12) United States Patent
van Dinther et al.

(10) Patent No.: US 10,034,639 B2
(45) Date of Patent: Jul. 31, 2018

(54) OPTICAL VITAL SIGNS SENSOR

(71) Applicant: KONINKLIJKE PHILIPS N.V., Eindhoven (NL)

(72) Inventors: Cornelus Hendricus Bertus Arnoldus van Dinther, Mierlo (NL); David Antoine Christian Marie Roovers, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 15/297,861

(22) Filed: Oct. 19, 2016

(65) Prior Publication Data

US 2017/0035362 A1    Feb. 9, 2017

Related U.S. Application Data

(63) Continuation of application No. PCT/EP2016/050013, filed on Jan. 4, 2016.

(30) Foreign Application Priority Data

Jan. 16, 2015    (EP) .................................... 15151374

(51) Int. Cl.
*A61B 5/024*    (2006.01)
*A61B 5/00*    (2006.01)
*A61B 5/11*    (2006.01)

(52) U.S. Cl.
CPC .......... *A61B 5/721* (2013.01); *A61B 5/02416* (2013.01); *A61B 5/02433* (2013.01); *A61B 5/1118* (2013.01); *A61B 5/11* (2013.01); *A61B 5/1116* (2013.01); *A61B 2560/0209* (2013.01); *A61B 2562/0238* (2013.01)

(58) Field of Classification Search
CPC .... A61B 2562/0219; A61B 2562/0233; A61B 5/02405; A61B 5/02416; A61B 5/02438; A61B 5/11; A61B 5/681; A61B 5/02055; A63B 2230/06
See application file for complete search history.

(56) References Cited

U.S. PATENT DOCUMENTS

| | | |
|---|---|---|
| 7,018,338 B2 | 3/2006 | Vetter et al. |
| 2003/0065269 A1 | 4/2003 | Vetter et al. |
| 2012/0203077 A1 | 8/2012 | He et al. |
| 2012/0203491 A1 | 8/2012 | Sun et al. |
| 2014/0073486 A1* | 3/2014 | Ahmed ............. A61B 5/02405 482/9 |

(Continued)

FOREIGN PATENT DOCUMENTS

| | | |
|---|---|---|
| EP | 2116183 B1 | 2/2012 |
| WO | 2015180986 A1 | 12/2015 |

*Primary Examiner* — Elmer Chao

(57) ABSTRACT

An optical vital signs sensor is provided which comprises at least one light source with a primary and a secondary light unit and a photo detector, a motion sensor configured to detect a motion of a user, a periodicity metric unit to analyze an output signal of the at least one motion sensor to detect a periodicity in its output signal and a control unit configured to control an operation of the at least one primary and secondary light unit and to activate the at least one secondary light unit in addition to the at least one primary light unit when the periodicity metric unit does not detect a periodicity in the output signal of the motion sensor.

15 Claims, 3 Drawing Sheets

(56) References Cited

U.S. PATENT DOCUMENTS

2014/0275854 A1  9/2014  Venkatraman et al.
2014/0288390 A1* 9/2014  Hong ................. A61B 5/02427
                                                600/301
2014/0323828 A1  10/2014 Ahmed et al.

* cited by examiner

OPTICAL VITAL SIGNS SENSOR

TECHNICAL FIELD

Various embodiments relate to an optical vital signs sensor and a method of operating an optical vital signs sensor.

BACKGROUND

Optical heart rate sensors are well known to monitor or detect vital signs like a heart rate of a user. Such a heart rate sensor can be based on a photoplethysmograph (PPG) sensor and can be used to acquire a volumetric organ measurement. By means of pulse oximeters, changes in light absorption of a human skin is detected and based on these measurements a heart rate or other vital signs of a user can be determined. The PPG sensors comprise a light source like a light emitting diode (LED) which is emitting light into the skin of a user. The emitted light is scattered in the skin and is at least partially absorbed by the blood. Part of the light exits the skin and can be captured by a photodiode. The amount of light that is captured by the photo diode can be an indication of the blood volume inside the skin of a user. A PPG sensor can monitor the perfusion of blood in the dermis and subcutaneous tissue of the skin through an absorption measurement at a specific wave length. If the blood volume is changed due to the pulsating heart, the scattered light coming back from the skin of the user is also changing. Therefore, by monitoring the detected light signal by means of the photodiode, a pulse of a user in his skin and thus the heart rate can be determined.

In other words, information regarding cardiovascular status like blood oxygen saturation, heart and respiratory rates can be unobtrusively acquired by a PPG sensor. However, PPG sensors can be susceptible to motion-induced signal distortions.

EP2116183 B1 discloses an opto-electrical ear located cardio vascular monitoring device which comprises two infrared light emitting devices emitting at two different wavelengths, wherein this light is detected by two pairs of photo diodes. Furthermore, the device comprises a motion sensor for detecting the motion of a user. If the user is at rest or is moving too irregularly, one of the cardio vascular sensors can be switched off. The usage of two different light emitting diodes will, however, increase the power consumption of the sensor.

SUMMARY

Various embodiments described herein provide an optical vital signs sensor which is able to efficiently detect vital signs of a user in particular when the user is in motion while still reducing the power consumption.

According to various embodiments, an optical vital signs sensor is provided which comprises at least one light source having at least one primary and at least one secondary light unit which are each configured to generate light, which is directed towards a skin of a user. The primary light unit is activated when the optical vital signs sensor is switched on. The optical vital signs sensor furthermore comprises at least one photo detector unit having at least one photo diode configured to detect light which is indicative of a transmission or reflection of the light from the at least one primary and at least one secondary light unit in or from the skin of a user. The optical vital signs sensor furthermore comprises at least one motion sensor configured to detect a motion of a user, a periodicity metric unit configured to analyze an output signal of the at least one motion sensor to detect a periodicity in its output signal and a control unit configured to control an operation of the at least one primary and secondary light unit. The control unit is configured to activate the at least one secondary light unit in addition to the at least one primary light unit when the periodicity metric unit does not detect a periodicity in the output signal of the motion sensor. Hence, the primary light unit (for example green) is always activated while the secondary light unit is only activated when required for example to enhance the robustness of the signal. If based on the output signal of the motion sensor any motion artifacts can be removed, the secondary light units are not activated. However, if the motion artifacts cannot be removed only based on the information from the motion sensor, the secondary light units are activated and the output signal from the photo detector relating to the light from the secondary light unit is also used.

According to various embodiments, the control unit comprises a motion artifact removal unit which is configured to remove motion artifacts from the output signal of the photo detector unit based on an output signal of the at least one motion sensor and an output signal of the at least one photo detector unit based on light from the at least one secondary light unit when the at least one secondary light unit is activated.

According to various embodiments, the at least one primary light unit emits green light and the at least one secondary unit emits red, yellow or infrared light.

According to various embodiments, the control unit is configured to activate the at least one secondary light unit with a predetermined delay if the periodicity metric unit has detected a periodicity in the output signal of the at least one motion sensor.

According to various embodiments, the primary light unit is configured to emit green light. In order to determine a resting of a person, the output signal of the photo diode detecting the green light from the primary light unit can be examined to determine the morphology. If a resting of a person is thus detected, the secondary sensors can be deactivated.

According to various embodiments, a method of operating an optical vital signs sensor having at least one light source having at least one primary and at least one secondary light unit, at least one photo detector unit having at least one photo detector and a motion sensor is provided. The primary light unit is activated to direct light towards a skin of a user when the optical vital signs sensor is switched on. A light is detected which is indicative of a transmission or reflection of the light from the at least one primary and/or at least one secondary light unit in or from the skin of a user. A motion of the user is detected by a motion sensor. An output signal of the at least one motion sensor is analyzed to detect a periodicity of the output signal. An operation of the at least one primary and/or at least one secondary light unit is controlled. The at least one secondary light unit is activated in addition to the at least one primary light unit when a periodicity is not detected in the output signal of the motion sensor.

According to various embodiments, an optical vital signs sensor having an accelerometer or motion sensor to detect a motion of the user as well as at least two PPG sensors each comprising a light source as well at least one photo detector. One sensor is the primary sensor and can use e.g. green light. The other sensor is a secondary sensor and may use another color like red, blue, yellow or infrared light.

Based on the results of the accelerometer in particular motion artifacts due to periodic motion of the sensors like walking, running or cycling can be efficiently removed from the output signal of the PPG sensors. This is due to a significant correlation between motion artifacts in the output signal of the PPG sensor and the output of the accelerometer. On the other hand, motion artifacts caused by an aperiodic motion and motion artifacts which cannot be sensed by the accelerometer (variations in sensor-skin contact or motion of the tendons below the skin cannot be removed efficiently) and can be removed when activating the secondary PPG sensor.

According to various embodiments, at least one further PPG sensor e.g. operating at a different color or emanating from a different sensor can be used to compensate for these kinds of motion artifacts. Thus, according to various embodiments, the usage of multi-channel PPG signals as well as signals from an accelerometer can be used to reduce motion artifacts from the output signal of a PPG sensor, thus making the entire sensing process more robust. A disadvantage of using multiple light sources and/or wavelengths is the resulting increase in power consumption and a reduction of battery lifetime.

According to various embodiments, additional PPG sensors can be turned off or deactivated when the output of the accelerometer is sufficient to remove artifacts from the output signal of the PPG sensors, wherein these artifacts are a result of movements.

According to various embodiments, some of the PPG sensors can be switched off or deactivated when the data from the accelerometer is sufficiently good to enable a removal of motion artifacts from the output signal of the still activated PPG sensor. Accordingly, one PPG sensor as primary sensor e.g. based on green light can be activated during the entire measuring process while additional PPG sensors can only be activated or switched on if the data from the accelerometer is not sufficient to enable the required removal of the motion artifacts in the output signals of the PPG sensor or PPG sensors.

These and other aspects will be apparent from and elucidated with reference to the embodiment(s) described hereinafter.

DETAILED DESCRIPTION OF EMBODIMENTS

Figure 1:
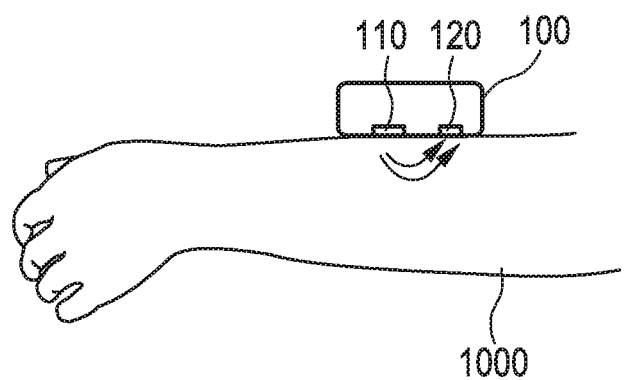
FIG. 1 shows a basic representation of an operational principle of an optical vital signs sensor.

FIG. 1 shows a basic representation of an operational principle of an optical heart rate sensor. In FIG. 1, a heart rate sensor is arranged on an arm of a user. The heart rate sensor 100 comprises a light source 110 and a photo detector 120 arranged at a fixed distance. The light source 110 emits light onto or in the skin 1000 of a user. Some of the light is reflected and the reflected light can be detected by the photo detector 120. The optical heart rate sensor can be embodied as a PPG sensor.

According to various embodiments, an optical vital signs sensor is provided which is based on a PPG sensor. Such PPG sensor is depicted in FIG. 1. A light source 110 emits light onto or into a skin 1000 of a user and some of this light is reflected and the reflected light can be detected by a photo detector 120. The output of the photo detector can be analyzed to determine a heart rate or other vital signs of a user.

The PPG sensor or optical vital signs sensor according to various embodiments can be implemented as a wrist device like a smart watch or as a finger-clip device. The PPG sensor according to various embodiments is wearable and is battery powered. In addition, the optical vital signs sensor according to various embodiments can also be implemented as a device which is e.g. worn behind the ear of the user or any parts of the user as long as it is ensured that the optical vital signs sensor is placed directly onto the skin 1000 of a user.

Figure 2:
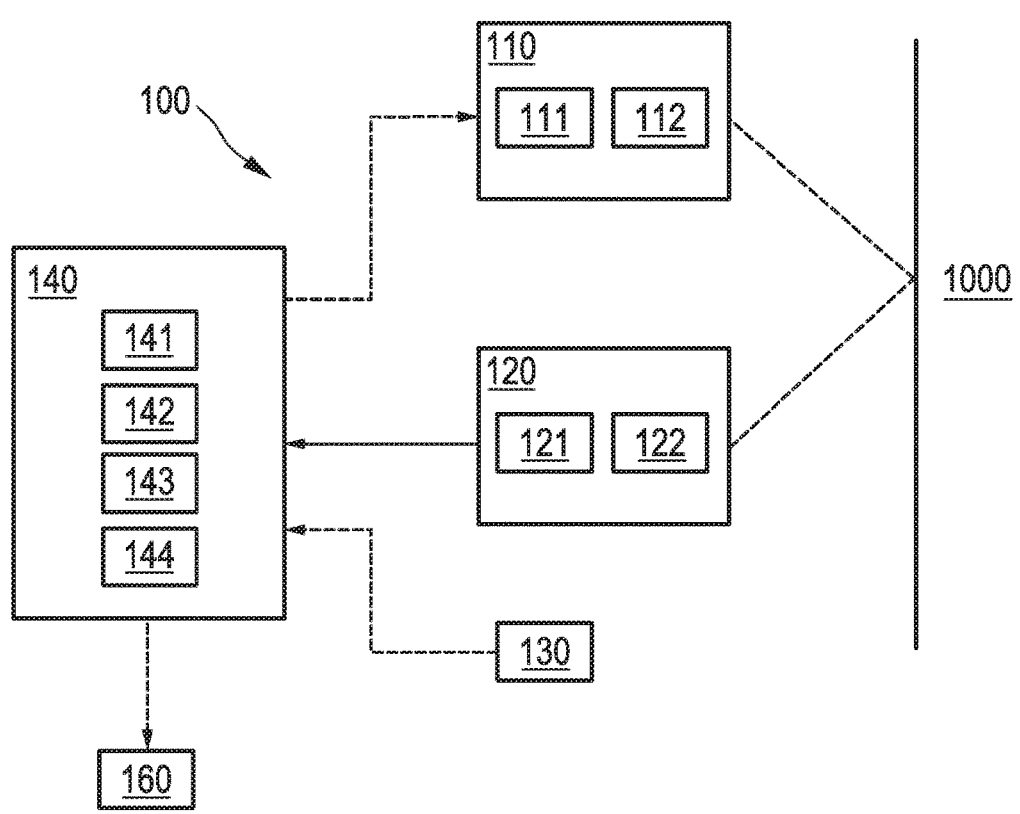
FIG. 2 shows a schematic block diagram of an optical vital signs sensor.

FIG. 2 shows a schematic block diagram of an optical vital signs sensor according to various embodiments. The optical vital signs sensor 100 comprises a light source 110 and a photo detector 120. The light source 110 emits light onto or in the skin 1000 of a user at a certain position and the photo detector 120 is able to detect reflected or transmitted light. The light source may comprise several light units 111, 112 which can e.g. be implemented as light emitting diodes LED or laser diodes and can emit light at different colors. In particular, at least one primary light unit 111 and at least one secondary light unit 112 is provided. The photo detector 120 may comprise at least one photo diode 121, 122 which serve to detect light as reflected or transmitted from the skin 1000 of a user.

The optical vital signs sensor 100 furthermore comprises a control unit 140 which can control the operation of the light source 110 and/or the photo detector 120. The optical vital signs sensor 100 furthermore comprises an accelerometer or a motion sensor 130. The control unit 140 can receive the output of the photo detector 120. The control unit 140 can also receive the output of the motion sensor 130. Optionally, the optical vital signs sensor 100 can comprise a display 160 for displaying vital signs such as a heart rate of a user. The control unit 140 can comprise a heart rate estimating unit 141, a motion artifact removal unit 142, a periodicity metric unit 143 and a switching unit 144.

According to various embodiments, the primary and secondary light units 111, 112 generate light at different wavelengths such that two independent output signals at the photo diodes of the photo detector are generated. In some embodiments, the two different light signals from the primary and secondary light units 111, 112 can be separated in the photo detector 120. This can be done by two different photo diodes or by time multiplexing. The primary and secondary light units 111, 112 can emit pulsed light. The detection of this light by the photo detector 120 can be synchronized with the emitted pulsed light. Thus, two colors can independently be detected.

Figure 3:
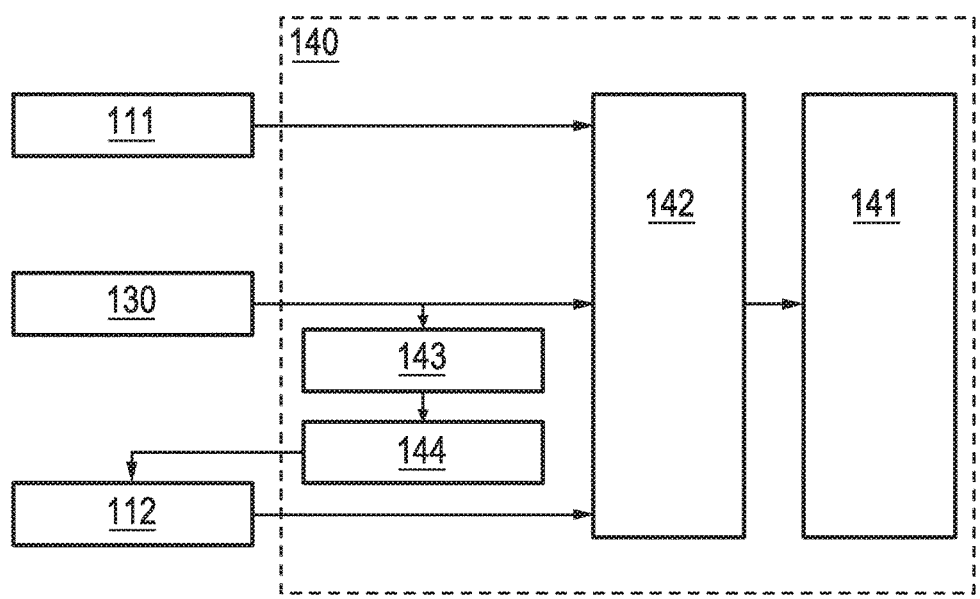
FIG. 3 shows a schematic block diagram of an optical vital signs sensor.

FIG. 3 shows a schematic block diagram of an optical vital signs sensor according to various embodiments. Here, the primary light unit 111 and the at least one secondary light unit 112 are shown together with the motion sensor 130.

The control unit 140 can comprise a heart rate estimation unit 141 and a motion artifact removal unit 142. The motion artifact removal unit 142 can receive the output signal of the photo detector 120 which is detecting the (reflected) light from the primary light unit 111, which can be implemented as a PPG sensor emitting e.g. green light. The motion artifact removal unit 142 can also receive the output signal of the motion sensor 130. The motion artifact removal unit 142 serves to remove artifacts from the output signal of the photo detector based on light from the first light unit 111 based on the output signal of the motion sensor 130.

The control unit 140 can also comprise a periodicity metric unit 143 as well as a switching unit 144. The periodicity metric unit 143 serves to detect a periodic motion in the output signal of the motion sensor 130. The switching unit 144 is coupled to the at least one secondary sensor 112 and serves to activate or deactivate the secondary light unit 112. The switching unit 144 is deciding to switch on or off the at least one secondary light unit 112 based on the output signal of the periodicity metric unit 143. The output of the motion artifact removal unit 142 corresponds to the output of the first PPG sensor 111 but without the motion artifact as removed by the motion artifact removal unit 142. Based on these signals, the heart rate estimating unit 141 can determine or estimate the heart rate of a user more efficiently and accurately.

The periodicity metric unit 143 determines the periodicity of the output signals of the motion sensor 130. Based on these results, the at least one secondary light unit 112 is activated or deactivated. The at least one secondary light unit 112 can be implemented as multi-color LEDs and can emit e.g. red, yellow and/or infrared light. In particular, the motion artifact removal unit 142 works well with periodic movements or motion. Thus, the additional secondary light unit 112 is not required and can thus remain deactivated thus reducing the power consumption.

If however aperiodic movements or motion is detected by the periodicity metric unit 143, the at least one secondary light unit 112 can be activated by the switching unit 144 and the output of the at least one secondary light unit 112 is forwarded to the motion artifact removal unit 142. These aperiodic movements can e.g. occur when there is no motion of the arm and thus no or only a reduced accelerometer signal.

Furthermore, it should be noted that the secondary PPG sensors or light units 112 can be multi-channel PPG sensors that may be used during ramp ups of the heart rate which may occur at the start of a periodic movement. According to various embodiments, the switching unit 144 or the control unit 140 can be adapted to introduce latency when switching off the second PPG sensors 112 in particular if a periodic motion is detected at the same time. If the periodic motion is stopped, then the at least one second PPG sensor 112 can be activated e.g. by means of the switching unit 144. Here, the motion artifacts are removed based on the combination of multi-channel PPG sensors and the signals of the accelerometer or the motion sensor.

According to a further aspect of the embodiment, the first PPG sensor which can emit green light can be used to detect a resting of a person. It should be noted that the output signal of a PPG sensor using green light can have a characteristic morphology. If from the output signal of the first PPG sensor it can be detected that a person is at rest, the second PPG sensors can be deactivated.

In addition, if a person is detected at being at rest e.g. based on the output signal of the first PPG sensor (green sensor), the motion artifact removal unit 142 can be deactivated.

The optical vital signs sensor according to various embodiments may also comprise at least two different PPG sensors each having a light unit and at least one photo diode wherein the PPG sensors can emit light at different colors. In this case, each PPG sensor can be a dedicated sensor having at least one light unit as well as at least one photo diode.

Other variations of the disclosed embodiment can be understood and effected by those skilled in the art in practicing the methods, systems, and principles described herein from a study of the drawings, the disclosure and the appended claims.

In the claims, the word "comprising" does not exclude other elements or steps and in the indefinite article "a" or "an" does not exclude a plurality.

A single unit or device may fulfill the functions of several items recited in the claims. The mere fact that certain measures are recited in mutual different dependent claims does not indicate that a combination of these measurements cannot be used to advantage. A computer program may be stored/distributed on a suitable medium such as an optical storage medium or a solid state medium, supplied together with or as a part of other hardware, but may also be distributed in other forms such as via the internet or other wired or wireless telecommunication systems.

Any reference signs in the claims should not be construed as limiting the scope.

The invention claimed is:

1. An optical vital signs sensor, comprising:
    at least one light source having at least one primary and at least one secondary light unit each being configured to generate light, which is directed towards a skin of a user, said primary light unit being activated when the optical vital signs sensor is switched on, wherein the primary light unit emits light of a first color and the secondary light unit emits light of a second color different from the first color,
    at least one photo detector unit having at least one photo diode configured to detect light which is indicative of a transmission or reflection of the light from the at least one primary and at least one secondary light unit in or from the skin of the user, wherein the at least one photodetector unit produces a detected light signal,
    at least one motion sensor configured to detect a motion of the optical vital signs sensor,
    a periodicity metric unit configured to analyze an output signal of the at least one motion sensor to determine whether or not the motion of the optical vital signs sensor is periodic,
    a switching unit configured to control an operation of the at least one primary and secondary light unit, wherein the switching unit is configured to:
        activate the at least one secondary light unit in addition to the at least one primary light unit when the periodicity metric unit determines that the motion is not periodic,
        deactivate the at least one secondary light unit when the periodicity metric unit determines that the motion is periodic,
        wherein the at least one primary light operates regardless of whether or not the motion is periodic, and
    a motion artifact removal unit configured to remove motion artifacts from the detected light signal of the photo detector unit based on:
        the output signal of the at least one motion sensor when the motion is determined to be periodic, and
        the detected light signal including detected light of the second color from the at least one secondary light unit when the at least one secondary light unit is activated.

2. Optical vital signs sensor according to claim 1, wherein the at least one primary light unit emits green light and/or the at least one secondary light unit emits red, yellow or infrared light.

3. An optical vital signs sensor according to claim 1, wherein the switching unit is configured to deactivate the at least one secondary light unit with a predetermined delay, if the periodicity metric unit has determined that the motion is periodic.

4. An optical vital signs sensor according to claim 1, wherein the periodicity metric unit is configured to detect a resting of a user of the optical vital signs sensor based on the output signal of the photo detector unit, wherein the switching unit is configured to deactivate the at least one secondary light unit if a resting of the user is determined.

5. An optical vital signs sensor according to claim 4, further comprising
a motion artifact removal unit which is configured to remove motion artifacts from the output signal of the photo detector unit, and
the switching unit is configured to deactivate the motion artifact removal unit if the periodicity metric unit has determined that a person is at rest.

6. Method of operating an optical vital signs sensor having at least one light source having at least one primary and at least one secondary light unit, at least one photo detector unit having at least one photo diode and a motion sensor, comprising the steps of:
activating a primary light unit to direct its light towards a skin of a user, when the optical vital signs sensor is switched on, wherein the primary light unit emits light of a first color and the secondary light unit emits light of a second color different from the first color,
detecting a light which is indicative of a transmission or reflection of the light from the at least one primary and/or at least one secondary light unit in or from the skin of the user,
detecting a motion of the optical vital signs sensor by a motion sensor,
analyzing an output signal of the at least one motion sensor to determine whether or not the motion of the optical vital signs sensor is periodic,
controlling an operation of the at least one primary light unit regardless of whether the motion is periodic,
activating the at least one secondary light unit in addition to the at least one primary light unit when the motion is determined to not be periodic;
deactivating the at least one secondary light unit when the motion is determined to be periodic; and
removing motion artifacts from the output signal based on the output signal of the motion sensor when the motion is determined to be periodic, and based on the detected light including detected light of the second color from the at secondary light unit when the at least one secondary light unit is activated.

7. The method according to claim 6, wherein the at least one primary light unit emits green light and/or the at least one secondary light unit emits red, yellow or infrared light.

8. The method according to claim 6, wherein the activating comprises deactivating the at least one secondary light unit with a predetermined delay, if motion is periodic.

9. The method according to claim 6, further comprising:
detecting a resting of a user of based on the detected light; and
deactivating the at least one secondary light unit if a resting of the user is determined.

10. The method according to claim 9, further comprising:
removing motion artifacts from the output signal of the photo detector unit, and
wherein the removing is omitted if the person is determined to be at rest.

11. A non-transitory machine-readable storage medium comprising instructions for execution by a processor, the medium comprising:
instructions for activating a primary light unit to direct its light towards a skin of a user, when the optical vital signs sensor is switched on, wherein the primary light unit emits light of a first color and a secondary light unit emits light of a second color different from the first color,
instructions for detecting a light which is indicative of a transmission or reflection of the light from the at least one primary and/or at least one secondary light unit in or from the skin of the user,
instructions for detecting a motion of the optical vital signs sensor by a motion sensor,
instructions for analyzing an output signal of the at least one motion sensor to determine whether or not the motion of the user is periodic,
instructions for controlling an operation of the at least one primary light unit regardless of whether the motion is periodic,
instructions for activating the at least one secondary light unit in addition to the at least one primary light unit when the motion is determined to not be periodic;
instructions for deactivating the at least one secondary light unit when the motion is determined to be periodic; and
instructions for removing motion artifacts from the output signal based on the output signal of the motion sensor when the motion is determined to be periodic, and based on the detected light including detected light of the second color from the at secondary light unit when the at least one secondary light unit is activated.

12. The non-transitory machine-readable storage medium according to claim 11, wherein the at least one primary light unit emits green light and/or the at least one secondary light unit emits red, yellow or infrared light.

13. The non-transitory machine-readable storage medium according to claim 11, wherein the instructions for activating comprise instructions for deactivating the at least one secondary light unit with a predetermined delay, if motion is periodic.

14. The non-transitory machine-readable storage medium according to claim 11, further comprising:
instructions for detecting a resting of a user of based on the detected light; and
instructions for deactivating the at least one secondary light unit if a resting of the user is determined.

15. The non-transitory machine-readable storage medium according to claim 14, further comprising:
instructions for removing motion artifacts from the output signal of the photo detector unit, and
wherein the instructions for removing are configured to not be executed if the person is determined to be at rest.

* * * * *